United States Patent
Philippe

[11] Patent Number: 5,889,047
[45] Date of Patent: Mar. 30, 1999

[54] N-(ALKYOXYCARBONYL)-N-(2-HYDROXY-3-ALKYLOXYPROPYL)-ETHANOLAMINE DERIVATIVES AND THEIR USE IN, AND FOR THE PREPARATION OF, COSMETIC OR DERMATOLOGICAL COMPOSITIONS

[75] Inventor: Michel Philippe, Wissous, France

[73] Assignee: L'Oreal, Paris, France

[21] Appl. No.: 910,743

[22] Filed: Aug. 13, 1997

[30] Foreign Application Priority Data

Aug. 14, 1996 [FR] France ................................. 96 10230

[51] Int. Cl.⁶ .......................... A01N 47/10; C07C 261/00
[52] U.S. Cl. ............................. 514/478; 560/160
[58] Field of Search ................... 560/160; 514/669, 514/670, 478

[56] References Cited

FOREIGN PATENT DOCUMENTS

| 0 227 994 | 7/1987 | European Pat. Off. . |
| 0 482 860 | 4/1992 | European Pat. Off. . |
| 0 666 251 | 8/1995 | European Pat. Off. . |

OTHER PUBLICATIONS

English Derwent Abstract of EP 0 666 251.

*Primary Examiner*—Brian M. Burn
*Assistant Examiner*—Brian J. Davis
*Attorney, Agent, or Firm*—Finnegan, Henderson Farabow, Garrett & Dunner, L.L.P.

[57] ABSTRACT

N-(alkyloxycarbonyl)-N-(2-hydroxy-3-alkyloxypropyl) ethanolamine derivatives corresponding to the following formula:

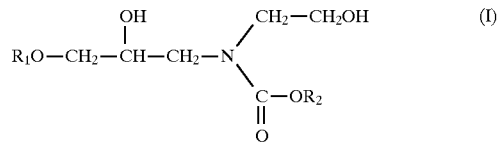

in which $R_1$ and $R_2$, which may be identical or different, represent a linear or branched, saturated or unsaturated and optionally hydroxylated alkyl radical having from 8 to 26 carbon atoms; as well as to their use in, and for the preparation of, cosmetic or dermatological compositions. These compositions are used in particular as moisturizers in skincare products or as conditioners in hair products.

13 Claims, No Drawings

N-(ALKYOXYCARBONYL)-N-(2-HYDROXY-3-ALKYLOXYPROPYL)-ETHANOLAMINE DERIVATIVES AND THEIR USE IN, AND FOR THE PREPARATION OF, COSMETIC OR DERMATOLOGICAL COMPOSITIONS

The invention relates to N-(alkyloxycarbonyl)-N-(2-hydroxy-3-alkyloxypropyl)ethanolamine derivatives as well as to their use in, and for the preparation of, cosmetic or dermatological compositions.

Exposure of the skin to cold, to sunlight, to atmospheres of low relative humidity, repeated treatments with washing compositions or contact of the skin with organic solvents are factors which lead, in varying degrees, to apparent drying. The skin appears drier and less flexible and the skin relief appears deeper. After having been subjected to repeated treatments, the hair also may lose its shiny appearance and become coarse and brittle.

It thus appeared to be desirable to be able to apply to the skin and/or the hair compositions which make it possible to prevent or correct these phenomena and thus to restore the skin's flexibility and the hair's softness and sheen.

In order to solve these problems, it has already been proposed to use lipophilic amides in cosmetic or dermatological compositions, in particular in patent applications EP-A-227,994, EP-A-482,860 and DE 43 26 959.

The inventor has discovered, surprisingly, that specific N-(alkyloxycarbonyl)-N-(2-hydroxy-3-alkyloxypropyl) ethanolamine derivatives whose structure will be defined below have advantageous cosmetic properties, in particular skin-moisturizing properties.

Indeed, it has been observed that by applying these products to the skin, it is possible to increase the fixing of water in the stratum corneum. These compounds may thus be used as moisturizers, in particular for human skin.

They make it possible to conserve or restore the skin's flexibility, its elasticity, its resistance to body movement and its function as a barrier to the entry of toxic substances. They may be used in care products for dry skins or skins with a predisposition towards dryness.

These compounds have, unexpectedly, an activity of fixing water in the stratum corneum which is substantially greater than that of the lipophilic amides known in cosmetics for their moisturizing properties.

The inventor has also discovered, surprisingly, that the specific N-(alkyloxycarbonyl)-N-(2-hydroxy-3-alkyloxypropyl)ethanolamine derivatives according to the invention, used in hair compositions, give the hair a particularly soft feel and facilitate its disentangling. They may be used as hair conditioners.

One subject of the invention relates to specific N-(alkyloxycarbonyl)-N-(2-hydroxy-3-alkyloxypropyl) ethanolamine derivatives, the structure of which will be indicated below.

Another subject of the invention relates to the use of the said N-(alkyloxycarbonyl)-N-(2-hydroxy-3-alkyloxypropyl)ethanolamine derivatives which will be defined below, in and for the preparation of cosmetic or dermatological compositions.

Another subject of the invention relates to the cosmetic or dermatological compositions containing these N-(alkyloxycarbonyl) -N-(2-hydroxy-3-alkyloxypropyl) ethanolamine derivatives.

Another subject of the invention thus relates to the use of these derivatives as moisturizers in, and for the preparation of, skincare compositions.

Another subject of the invention relates to the use of these N-(alkyloxycarbonyl)-N-(2-hydroxy-3-alkyloxypropyl)ethanolamine derivatives as hair conditioners in, and for the preparation of, hair compositions.

The N-(alkyloxycarbonyl)-N-(2-hydroxy-3-alkyloxy-propyl)ethanolamine derivatives in accordance with the invention correspond to the general formula (I) below:

$$R_1O-CH_2-CH(OH)-CH_2-N(CH_2-CH_2OH)(C(=O)-OR_2) \quad (I)$$

in which $R_1$ and $R_2$, which may be identical or different, represent a linear or branched, saturated or unsaturated and optionally hydroxylated alkyl radical having from 8 to 26 carbon atoms, preferably from 10 to 16 carbon atoms.

Among the preferred compounds corresponding to the general formula (I), mention may be made in particular of:

N-(hexadecyloxycarbonyl)-N-(2-hydroxy-3-hexadecyloxypropyl) ethanolamine

N-(dodecyloxycarbonyl)-N-(2-hydroxy-3-hexadecyloxypropyl) ethanolamine

N-(2-ethylhexyloxycarbonyl)-N-(2-hydroxy-3-hexadecyloxypropyl) ethanolamine.

These compounds may be obtained by alkyloxycarbonylation of the amine function of a compound of formula (II) below:

$$R_1O-CH_2-CH(OH)-CH_2-NH(CH_2-CH_2OH) \quad (II)$$

in which $R_1$ has the same meanings indicated above, by reacting in an organic solvent (preferably tetrahydrofuran), this compound with a compound of formula (III) below:

$$R_2O-C(=O)-A \quad (III)$$

in which:

A is an activating group chosen from a halogen atom such as chlorine and an azolide such as the imidazolide residue of structure:

[imidazolide structure]

$R_2$ has the same meanings indicated above, and then in adding an organic base such as triethylamine to the reaction medium.

The synthesis of the compounds of the invention is generally carried out according to conventional methods such as those described in the document "Advanced Organic Chemistry" edited by J. March.

The starting compounds of formula (II) are known and described in particular in Polish Journal of Chemistry, 52, 1283 and in application EP-A-227,994.

The cosmetic or dermatological compositions according to the invention are characterized in that they contain, in a cosmetically or dermatologically acceptable vehicle, at least one compound of formula (I) as defined above.

The cosmetic or dermatological compositions according to the invention preferably comprise 0.001 to 15% by weight of compound of formula (I) relative to the total weight of the composition.

The cosmetically acceptable vehicle used in the compositions of the invention is chosen from water; organic solvents which are compatible with a skin or hair application such as acetone, isopropanol and ethanol; triglycerides of fatty acids containing 6–24 carbon atoms, glycol ethers, polyalkylene glycol esters and volatile silicones or mixtures thereof.

The compositions may be in the form of a monophasic or polyphasic aqueous or aqueous-alcoholic lotion, a monophasic or polyphasic gel, an emulsion, a cream or a vesicle dispersion of ionic or nonionic lipids, it being possible for the said vesicles then to serve as encapsulating agents for lipophilic or hydrophilic active ingredients, a mousse or a spray.

The skincare compositions according to the invention may be in the form of a lotion, a gel, an emulsion, a cream or a mousse to be applied to the skin.

The hair compositions may be in the form of a shampoo, a rinse-out or leave-in conditioner, permanent-wave, straightening, dyeing or bleaching compositions, or alternatively in the form of rinse-out compositions, to be applied before or after dyeing, permanent-waving or straightening the hair, or alternatively between the two steps of a permanent-waving or hair-straightening operation.

The cosmetic or dermatological compositions may moreover contain conventional cosmetic additives chosen from fatty substances, organic solvents, silicones, thickeners, softeners, surfactants, anionic, cationic, nonionic or amphoteric polymers, antifoaming agents, hair conditioners such as proteins, vitamins, treating agents (agents for preventing hair loss or antidandruff agents), dyes, fragrances, preserving agents and propellants.

More precisely, an oil or a wax or a mixture thereof, fatty acids, fatty alcohols, fatty acid esters such as triglycerides of $C_6$ to $C_{18}$ fatty acids, petroleum jelly, paraffin, lanolin, or hydrogenated or acetylated lanolin may be used as fatty substance.

Among the oils, mention may be made of mineral, animal, plant or synthetic oils, and in particular liquid petroleum jelly, liquid paraffin, castor oil, jojoba oil and sesame oil, as well as silicone gums and oils and isoparaffins.

Among the waxes, mention may be made of animal, plant, mineral or synthetic waxes, and in particular beeswax, candelilla wax, ozokerites, microcrystalline waxes and silicone waxes and resins.

Among the organic solvents usually used in the cosmetic compositions, mention may be made more precisely of $C_1$ to $C_6$ lower monoalcohols or polyalcohols such as ethanol, isopropanol, ethylene glycol, diethylene glycol, propylene glycol or glycerol.

The thickeners may be chosen in particular from sodium alginate, gum arabic, cellulose derivatives such as methylcellulose, hydroxymethylcellulose, hydroxyethylcellulose, hydroxypropylcellulose or hydroxypropylmethylcellulose, guar gum or derivatives thereof, xanthan gum, scleroglucans and crosslinked polyacrylic acids.

As surfactants and as polymers, use may be made of all those which are well known in the state of the art, in particular for their use in hair compositions.

The compositions may be in the form of a vesicle dispersion of ionic or nonionic amphiphilic lipids. They are prepared in particular by swelling the lipids in an aqueous solution in order to form spherules that are dispersed in the aqueous medium, as described in Standish & Watkins, J. Mol. Biol., 13,238 (1965) or in patents FR-A-2,315,991 and FR-A-2,416,008 by the inventors. The various types of preparation process are described in "Les liposomes en biologie cellulaire et pharmacologie" [Liposomes in cell biology and pharmacology], INSERM/John Libery Eurotext publication, 1987, pages 6 to 18.

The pH of the compositions according to the invention generally ranges from 4 to 8 and preferably from 5 to 7.

Several examples of the preparation of compounds according to the invention and examples of cosmetic compositions containing them will now be given by way of illustration and with no limiting nature.

EXAMPLE 1

Synthesis of N-(hexadecyloxycarbonyl)-N-(2-hydroxy-3-hexadecyloxypropyl)ethanolamine of formula (I) ($R_1=C_{16}H_{33}$, $R_2=C_{16}H_{33}$)

37 g ($10.3 \times 10^{-2}$ mol) of N-(2-hydroxypropyl-3-hexadecyloxy)ethanolamine are dissolved in 400 ml of warm tetrahydrofuran. 31.4 g ($10.3 \times 10^{-2}$ mol) of cetyl chloroformate in 100 ml of tetrahydrofuran are added dropwise. The reaction is slightly exothermic.

15 ml ($10.3 \times 10^{-2}$ mol) of triethylamine are then run in. The heterogeneous medium is heated for 30 min at 50° C. The absence of amine is checked by TLC.

After cooling to room temperature, 500 ml of water are added. The precipitate formed is filtered off, washed with water and then dried.

63.6 g of a white solid are obtained (yield=98%).

Elemental analysis:

|  | C | H | N | O |
|---|---|---|---|---|
| Calculated (%) | 72.67 | 12.36 | 2.23 | 12.74 |
| Found (%) | 72.71 | 12.40 | 2.24 | 12.89 |

TLC (eluent=9/1 dichloromethane/methanol): single spot Rf equal to about 0.5

200 MHz $^1$H NMR spectrum in agreement

Melting point (capillary): 72°–73° C.

EXAMPLE 2

Synthesis of N-(dodecyloxycarbonyl)-N-(2-hydroxy-3-hexadecyloxypropyl)ethanolamine of formula (I) ($R_1=C_{16}H_{33}$; $R_2=C_{12}H_{25}$)

50 g ($13.9 \times 10^{-2}$ mol) of N-(2-hydroxypropyl-3-hexadecyloxy)ethanolamine are dissolved in 500 ml of warm tetrahydrofuran. 34.6 g ($13.9 \times 10^{-2}$ mol) of dodecyl chloroformate in 100 ml of tetrahydrofuran are added dropwise. The temperature reaches 45° C.

19.3 ml ($13.9 \times 10^{-2}$ mol) of triethylamine are added. The heterogeneous medium is heated for 30 min at 50° C. The absence of amine is checked by TLC. After cooling to room temperature, 500 ml of water are added, the mixture is cooled and 400 ml of acetone are then added. The precipitate formed is filtered off and washed with acetone cooled to 5° C.

71.5 g of a white solid are obtained (yield=74%). The product is recrystallized from ethyl acetate and 59.1 g of white crystals are obtained.

Elemental analysis:

|  | C | H | N | O |
|---|---|---|---|---|
| Calculated (%) | 71.40 | 12.16 | 2.45 | 13.99 |
| Found (%) | 71.39 | 12.24 | 2.46 | 14.12 |

TLC (eluent=9/1 dichloromethane/methanol): single spot Rf equal to about 0.5
200 MHz $^1$H NMR spectrum in agreement
Melting point (capillary): 55–56° C.

EXAMPLE 3

Synthesis of N-(2-ethylhexyloxycarbonyl)-N-(2-hydroxy-3-hexadecyloxypropyl)ethanolamine of formula (I) ($R_1$=$C_{16}H_{33}$; $R_2$ =$CH_3$—$(CH_2)_3$—$CH(C_2H_5)$—$CH_2$—)

50 g ($13.9 \times 10^{-2}$ mol) of N-(2-hydroxypropyl-3-hexadecyloxy)ethanolamine are dissolved in 500 ml of warm tetrahydrofuran.

26.7 g ($13.9 \times 10^{-2}$ mol) of 2-ethylhexyl chloroformate are added dropwise. The reaction is slightly exothermic. 19.3 ml ($13.9 \times 10^{-2}$ mol) of triethylamine are then added. The heterogeneous medium is heated for 30 min at 50° C.

The absence of amine is checked by TLC. After cooling to room temperature, 500 ml of water are added and the mixture is extracted with 800 ml of dichloromethane. The organic phase is washed with sodium chloride solution. The organic phase is dried with sodium sulphate and evaporated to dryness. The liquid obtained is purified by chromatography.

62.6 g of a colourless liquid are obtained (yield=84%).
Elemental analysis:

|  | C | H | N | O |
|---|---|---|---|---|
| Calculated (%) | 69.86 | 11.92 | 2.72 | 15.51 |
| Found (%) | 69.20 | 11.85 | 3.04–3.20 | 15.53–15.80 |

TLC (eluent=9/1 dichloromethane/methanol): single spot Rf equal to about 0.5
200 MHz $^1$H NMR spectrum in agreement

EXAMPLE 4

Comparative example
Measurement of the skin conductivity

This measurement makes it possible to demonstrate the variation in the level of moisturization of the skin. It is carried out using apparatus which includes a central electrode in the form of a rod surrounded by a cylindrical electrode. The apparatus is applied to the skin and a high frequency alternating current is applied. It is observed that the more moisturized the skin, the larger is the amount of current consumed. The increase in skin conductivity and thus the increase in its level of moisturization is thus demonstrated.

This measurement is carried out for:
  a) N-(dodecyloxycarbonyl)-N-(2-hydroxy-3-hexadecyloxy-propyl) ethanolamine (compound of Example 2);
  b) N-dodecanoyl-N-(2-hydroxy-3-hexadecyloxypropyl) ethanolamine, amide homologue known in application EP-A-227,994 to be a moisturizing agent, which will be referred to as reference A.

The compound of Example 2 and that of reference A are prepared in a proportion of 3% in a dichloromethane/methanol mixture (2/1 by volume) and are then applied to samples of defatted stratum corneum.

The conductivity of the stratum corneum is measured, 20 hours after the application, for each compound.

The following results are obtained:

| Compound | Example 2 | Reference A |
|---|---|---|
| Conductivity | +44 +/−14 | −14 +/−8 |

EXAMPLE 5

Shampoo

| | |
|---|---|
| Alkyl ($C_9$/$C_{10}$/$C_{11}$-20/40/40) polyglucoside (1,4) sold under the name "APG 300" by Henkel, containing 50 g % active material (AM) | 15 g AM |
| N-(Dodecyloxycarbonyl)-N-(2-hydroxy-3-hexadecyloxypropyl)ethanolamine (compound of Example 2) | 2 g |
| Preserving agents, fragrance | qs |
| Water | qs 100 g |

This shampoo has the appearance of a clear liquid. It has a good foaming power and provides dried hair with softness and control.

EXAMPLE 6

Conditioner

| | |
|---|---|
| Behenyltrimethylammonium chloride at a concentration of 80% by weight in a water/isopropanol mixture (15/85) sold under the name "Catinal DC 80" by Toho | 2 g AM |
| N-(2-Ethylhexloxycarbonyl)-N-(2-hydroxy-3-hexadecyloxypropyl)ethanolamine (compound of Example 3) | 0.5 g |
| Preserving agents, fragrance | qs |
| Water | qs 100 g |
| Spontaneous pH 7.2 | |

This conditioner has the appearance of an opalescent liquid. When applied to the hair, it improves the disentangling of wet hair as well as the softness and control of dried hair.

EXAMPLE 7

Moisturizing day cream

| | |
|---|---|
| N-(Hexadecyloxycarbonyl)-N-(2-hydroxy-3-hexadecyloxypropyl)ethanolamine (compound of Example 1) | 0.5 g |
| Glyceryl stearate | 2.5 g |
| Mineral oil | 6.2 g |
| Isopropyl myristate | 3 g |
| Cetyl alcohol | 7 g |
| PEG-50 stearate | 2.5 g |
| Preserving agent | 0.3 g |
| Water | qs 100 g |

A day cream is obtained in the form of an emulsion which makes it possible to cover and protect the skin well, this emulsion being particularly suitable for normal and dry skins and proves to be moisturizing to the skin.

EXAMPLE 8

Moisturizing facial make-up base

| | |
|---|---|
| Mixture of cetearyl octanoate and isopropyl myristate | 2 g |
| N-(Dodecyloxycarbonyl)-N-(2-hydroxy-3-hexadecyloxypropyl)ethanolamine (compound of Example 2) | 0.5 g |

-continued

| | |
|---|---|
| Mineral oil | 7.5 g |
| Mixture of glyceryl stearate and PEG-100 stearate | 2 g |
| Stearic acid | 1.4 g |
| Cetyl alchol | 0.1 g |
| Hexyldecanol | 1 g |
| Glycerol | 3 g |
| Triethanolamine | 1.05 g |
| Carbomer sold under the brand name Carbopol | 0.35 g |
| Preserving agent | qs |
| Water | qs 100 g |

EXAMPLE 9

Moisturizing night cream for the skin

| | |
|---|---|
| Mixture of cetearyl octanoate and isopropyl myristate | 2 g |
| N-(2-Ethylhexyloxycarbonyl)-N-(2-hydroxy-3-hexadecyloxypropyl)ethanolamine (compound of Example 3) | 0.5 g |
| Glycerol | 10 g |
| Cellulose gum | 0.5 g |
| Polyethylene | 0.5 g |
| Magnesium sulphate | 0.65 g |
| Cyclomethicone | 15.36 g |
| Mixture of polyglyceryl-4 isostearate, cetyldimethicone copolyol and hexyl laurate | 4 g |
| Preserving agent | qs |
| Water | qs 100 g |

A night cream is obtained in the form of an emulsion which makes it possible to cover and protect the skin well, this cream being particularly suitable for normal and dry skins.

We claim:

1. A compound of the formula I:

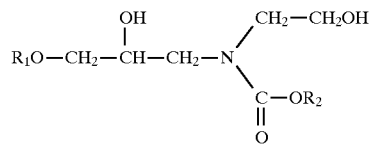

wherein $R_1$ and $R_2$, which may be identical or different, represent a linear or branched, saturated or unsaturated and optionally hydroxylated alkyl radical having from 8 to 26 carbon atoms.

2. A compound according to claim 1 wherein said compound is selected from N-(hexadecyloxycarbonyl)-N-(2-hydroxy-3-hexadecyloxypropyl)ethanolamine; N-(dodecyloxycarbonyl)-N-(2-hydroxy-3-hexadecyloxypropyl)ethanol-amine; and N-(2-ethylhexyloxycarbonyl)-N-(2-hydroxy-3-hexadecyloxypropyl)ethanolamine.

3. A process for preparation of a compound according to claim 1, comprising the steps of:

contacting, in the presence of an organic solvent, a compound of formula (II) below:

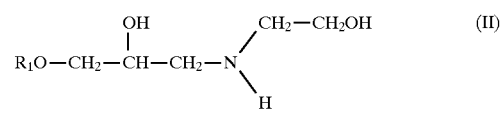

wherein $R_1$ has the same meanings according to claim 1, with a compound of formula (III) below:

wherein:

A is an activating group selected from a halogen atom and an azolide;

$R_2$ is defined as in claim 1; and, thereafter adding an organic base in an amount sufficient to obtain said compound according to claim 1.

4. A process comprising the step of including a compound according to claim 1 in a composition to form a cosmetic or dermatological composition.

5. A process comprising the step of including a compound according to claim 1 as a moisturizing agent in a composition to form a cosmetic or dermatological skincare composition.

6. A process comprising the step of including a compound according to claim 1 as a hair conditioner in a composition to form a hair composition.

7. A cosmetic or dermatological composition comprising at least one compound of formula (I) according to claim 1.

8. A composition according to claim 7 wherein said composition further comprises a cosmetically acceptable or dermatologically acceptable vehicle.

9. A composition according to claim 7, wherein said at least one compound is selected from N-(hexadecyloxycarbonyl)-N-(2-hydroxy-3-hexadecyloxypropyl)ethanolamine; N-(dodecyloxycarbonyl)-N-(2-hydroxy-3-hexadecyloxypropyl)ethanolamine; and N-(2-ethylhexyloxycarbonyl)-N-(2-hydroxy-3-hexadecyloxypropyl)ethanolamine.

10. A composition according to claim 7 wherein said at least one compound comprises from 0.001 to 15% by weight relative to the total weight of said composition.

11. A composition according to claim 7 wherein said composition is in the form of a monophasic or polyphasic aqueous or aqueous-alcoholic lotion, a monophasic or polyphasic gel, an emulsion, a cream, a mousse, a spray or a vesicle dispersion of ionic or nonionic lipids, wherein said vesicles may serve as encapsulating agents for lipophilic or hydrophilic active ingredients.

12. A composition according to claim 7 wherein said composition further comprises conventional cosmetic additives selected from fatty substances, organic solvents, silicones, thickeners, softeners, surfactants, anionic, cationic, nonionic and amphoteric polymers, antifoaming agents, hair conditioners, vitamins, treating agents, dyes, fragrances, preserving agents and propellants.

13. A composition according to claim 12 wherein said hair conditioners are proteins and further wherein said treating agents are selected from agents for preventing hair loss and antidandruff agents.

* * * * *